United States Patent [19]
Kreinick

[11] Patent Number: 4,762,518
[45] Date of Patent: Aug. 9, 1988

[54] BLOCKAGE HAZARD ALARM IN AN INTRAVENOUS SYSTEM

[75] Inventor: Stephen J. Kreinick, San Diego, Calif.

[73] Assignee: Pancretec, Inc., San Diego, Calif.

[21] Appl. No.: 892,318

[22] Filed: Aug. 1, 1986

[51] Int. Cl.[4] .................. A61M 5/005; G01N 15/06
[52] U.S. Cl. ........................... 604/245; 604/31; 604/65; 250/577
[58] Field of Search ............ 250/571, 577; 356/135; 128/DIG. 13; 604/122, 31, 245, 65

[56] References Cited

U.S. PATENT DOCUMENTS

| | | | |
|---|---|---|---|
| 2,350,712 | 6/1944 | Barsties | 250/577 |
| 2,383,347 | 8/1945 | Silge | 356/135 |
| 3,120,125 | 2/1964 | Vasel | 250/577 |
| 4,358,202 | 11/1982 | Puffer et al. | 250/571 |
| 4,416,541 | 11/1983 | Studer | 250/571 |
| 4,559,454 | 12/1985 | Kramer | 604/122 |

FOREIGN PATENT DOCUMENTS

84/04685  12/1984  PCT Int'l Appl. .................. 604/31

*Primary Examiner*—Stephen C. Pellegrino
*Assistant Examiner*—Ralph Lewis
*Attorney, Agent, or Firm*—Selwyn S. Berg

[57] ABSTRACT

The principal of total internal reflection is utilized in sounding an alarm in a medical fluid infusion system when a downstream blockage occurs. A miniature prism is mounted in a cavity in a rigid exterior tube. The infusing fluid flows in a plastic tubing along the central channel of the rigid tube. The plastic tubing in the interior of this exterior rigid tube is diametrically expansive with an unpressurized outside diameter which is less than the inside diameter of said rigid exterior tube. A light source and light detector is positioned adjacent to the equilateral planes of the prism mounted in the rigid tube. When an overpressure caused by a downstream blockage in the infusion system occurs, the inner expansive tubing distends diametrically and contacts the hypotenuse plane of the prism causing the light incident on the hypotenuse plane to change from the reflective mode to the refractive mode which interrupts the signal received by the light detector which is located adjacent to one of the equilateral planes of the prism which would project the light ray out of the prism when the system operates in the reflective mode.

1 Claim, 1 Drawing Sheet

BLOCKAGE HAZARD ALARM IN AN INTRAVENOUS SYSTEM

BACKGROUND

A major life threatening hazard associated with intravenous infusion systems is a blockage which prevents the infusion of the life saving media. Many monitoring systems exist to detect this hazard. Typical systems available work by mechanical linkages and changes in optical transmisivity. The system described herein uses the concept of total internal reflection by devices to be described in more detail. A major use of the phenomena of internal reflection is for light intensity modulation. However, it has also been used for liquid level detection, for pure fluid annunciator, and for fine measurement of pressure. The physics of total internal reflection is well described in the Patent of Whitsel (U.S. Pat. No. 3,517,639). Given: an isosceles triangular prism with two equilateral planes and its adjacent hypotenuse plane; for the sake of discussion, assume the prism is a right triangular glass prism. A light source is positioned so as to be incident normally on one of the perpendicular equilateral plane faces of the right angle prism. This means that the transmission of light rays will be incident on hypotenuse at an angle of substantially 45°. Accordingly, Snell's Law may be written as $n \sin\theta$ is $= n' \sin\theta'$ where n and n' are the indices of refraction of the prism material and the media present against the hypotenuse plane, and $\theta$ and $\theta'$ are the angles of incidence and refraction respectively. To find the critical angle which the refracted rays have an angle of 90°, that is $\theta'$ is $=90°$, it would follow the equation would be $\sin\theta_C = n'/n$, where $\theta_C$ is the critical angle. If the glass prism has an index of refraction of 1.5, and air is in contact with the hypotenuse plane, air having an index refraction of 1.00, the critical angle, $\theta_C$ for air is 42°. Light incident at 45° will be totally reflected in the prism to the other equilateral plane surface. If a plastic material makes contact with the hypotenuse plane, the critical angle changes. For example, if the index of refraction of the plastic is 1.33, the critical angle $\theta_C$ becomes 62°. Since the incident ray is set at 45°, which is less than the required incident angle of 62°, all of the incoming light will be refracted through the hypotenuse plane into the plastic and no light rays will be reflected through the other equilateral planes surface.

SUMMARY OF THE INVENTION

In the embodiment of this concept, a small right angle isosceles triangular optical prism is used in the blockage detector device. The prism set in a cavity in a rigid plastic tubing which is about the same diameter as the standard flexible intravenous tubing and the rigid tubing is attached by a nipple to the inside diameter of said flexible tubing. In this blockage detector there is a precalibrated diametrically expanding tubing in the central channel along the axis through which the media flows. Outside and adjacent to the expansive tubing in the central channel, the triangular glass prism is held in a cavity in the outer rigid plastic tubing with the hypotenuse plane of the prism facing toward the expansive tubing in the central channel. The expansive tubing in the central channel in its relaxed position does not make contact with the hypotenuse plane of the prism. Said expansive tubing is in a relaxed position if there is not adequate pressure to cause it to expand. On one of the equilateral plane surfaces of the prism is a light source transducer, and, on the other equilateral plane surface is a light detector transducer. The central channel expansive tubing is chosen to have an index of refraction which is compatible with Snell's Equation thus assuring the light rays will be coupled into the expansive tubing. If an occlusion occurs downstream of the blockage detector, the expanding tubing in the central channel would touch the prism and cause the light to be switched from reflecting to the detector and instead be refractively coupled into the expansive tubing of the central channel. Appropriate circuitry acting in concert with the light transducing detector would annunciate an alarm. This system is simple, rugged, low cost, and capable of being sterilized. Because there are no mechanically linked moving parts, it is highly dependable. The electronic circuitry including light sources and detector transducers are also known to be very dependable.

DESCRIPTION OF THE PREFERRED EMBODIMENT

Figure 1:
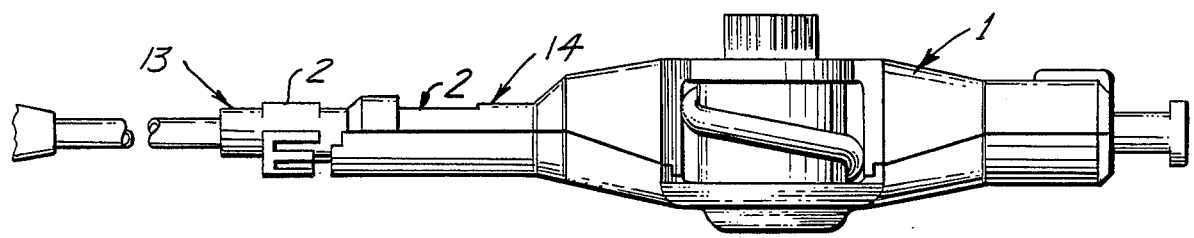
FIG. 1 is a top view of the peristaltic pump with its detector system on the output.
Figure 3:
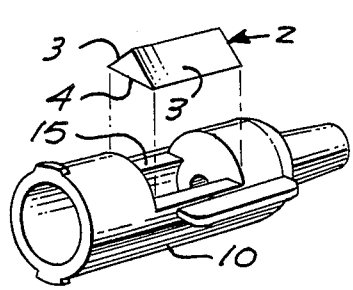
FIG. 3 shows the basic prism structure in the rigid plastic tubing.
Figure 4:
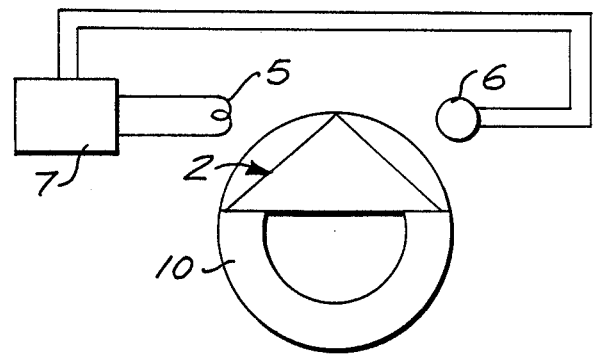
FIG. 4 shows a block diagram of the source and detector circuitry.

The above described system is illustrated in the figures. The intravenous tubing carries media, 8, into a peristaltic pump, 1, through the blockage detector, 14, as shown in FIG. 1. In the blockage detector there is an isosceles triangular prism, 2. FIG. 3 shows the mechanical structure in the rigid tubing cavity; the prism is comprised of two equilateral planes, 3, and one hypotenuse plane, 4. The hypotenuse plane is set into a cavity, 15, in the rigid plastic tubing, 10, so it faces the central channel through which media flows. To the side of one of the equilateral planes is a light source transducer, 5, and to the other side of the complimentary equilateral plane is a light detector transducer, 6. There is appropriate circuitry, 7, for power supply, amplifiers, and signal logic, as shown in FIG. 4.

By selecting a right angle isosceles triangular prism, an incident angle of 45° is easily established. If air is present on the active surface of the hypotenuse plane, the critical angle is exceeded, since 45° is larger than 42° and the light ray will be reflected causing the detector to be illuminated. If plastic is in contact with the hypotenuse plane, the critical angle of 62° is not exceeded and the light ray will be refracted into the plastic. Since no light will be reflected, the detector transducer will not be illuminated.

Figure 2:
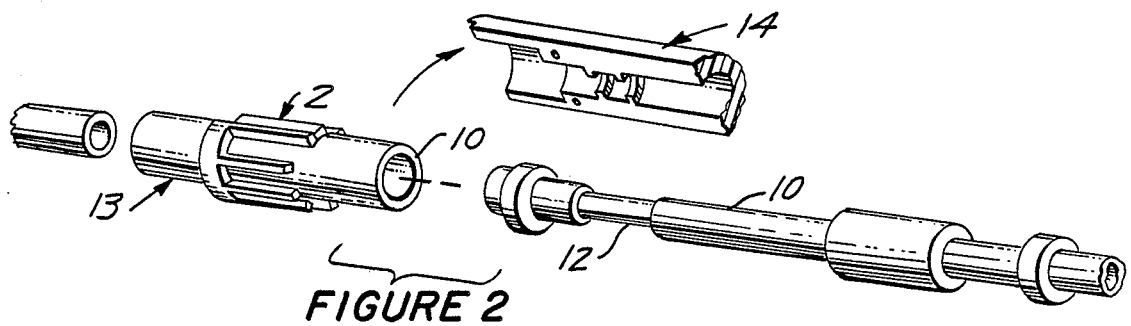
FIG. 2 is a blowup of the detector section showing the internal components of the blockage detector.
Figure 5:
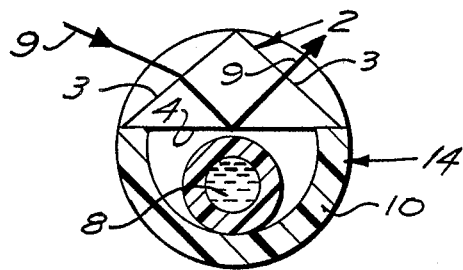
FIG. 5 shows the light rays in the reflective mode.
Figure 6:
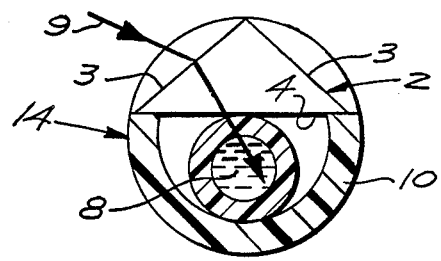
FIG. 6 shows the light rays in the refractive mode when the expansive tubing distends under increased pressure.

In the blockage detector, as shown in the FIG. 2 blowup, there is expansive plastic tubing in the central channel 12. This plastic tubing has been calibrated for diametrical expansion Experiments were performed on tubing of various diameters and wall thicknesses and plotted as the percentage change in diameter versus pressure. Selecting a particular tubing from these experiments and having the knowledge of its index of refraction, a combination of tubing and prism geometry maybe chosen so that when an over-pressure exists, the surface of the expansive tubing 12, in the central channel contacts the hypotenuse plane, 4, of the prism causing the light ray, 9, to be refracted out of the prism and away from the light detector transducer, 6. The change of state from the reflecting mode to the refracting mode is shown in FIGS. 5 and 6 respectively. If a silicone plastic is used as the expansive tubing, because its index of refraction being almost equal to water, a right angle isosceles triangular prism may be used.

FIG. 5 illustrates the path of a light ray, 9, reflecting from the hypotenuse, 4, when the expansive tubing of the central channel is in its relaxed position. In FIG. 6, the incident light ray, 9, is shown refracted from the hypotenuse plane, 4, through the expansive tubing and into the media, 8, when the expansive tubing makes contact with the hypotenuse plane of the prism. The diametrical distension of the expansive tubing is related to the over pressure existing in the media in the central channel in accordance with the geometrical characteristics of said expansive tubing as determined in calibration experiments. FIG. 4 illustrates the relative locations of the light source, 5, and the light detector, 6, and a box diagram showing of associated logic, 7, which will sound the alarm under appropriate conditions.

Though the described embodiment indicates this alarm device is incorporated in the effluent arm of a peristaltic pump, it is anticipated that the alarm may be incorporated into independent devices placed on-line with medical media infusion systems.

I claim:

1. A medical infusion blockage alarm system comprising an external flexible conduit tubing,
   a rigid tubing,
   a central channel,
   connecting means,
   and internal expansive plastic tubing with an index of refraction close to that of water,
   an optical prism of a high index of refraction,
   a light source,
   a light detector,
   alarm means said external flexible conduit being connected to said rigid tubing forming interiorly and concentrically said central channel and in said central channel, a length of said internal expansive plastic tubing containing a flowing liquid and attached by said connecting means to the interior of said rigid tubing and said expansive plastic tubing having an outside diameter which is less than the inside diameter of said rigid tubing so that an air space exists between the exterior of said expansive plastic tubing when it is not in an expanded state, said rigid tubing having a cavity created in its wall to hold said optical prism, said optical prism having two equilateral planes and one hypotenuse plane,
   where said hypotenuse plane is adjacent but not in contact with said internal expansive plastic tubing through which said liquid flows in said central channel and
   said light source interfacing one of said equilateral planes and said light detector interfacing with other said equilateral plane with said alarm means connected to said light detector and said light source so that light rays emitted from said source enters said first equilateral plane, illuminates said hypotenuse plane and is reflected from said hypotenuse plane to penetrate other said equilateral plane to illuminate said light detector, but if said internal expansive plastic tubing is diametrically enlarged because of some excessive internal pressure of said liquid in said central channel, a wall of said internal expansive plastic tubing contacts said hypotenuse plane causing the light of said source to refract out of said illuminated hypotenuse plane, interrupting the illumination of said light detector thereby terminating a signal to cause said alarm means to sound.

* * * * *